US008642305B2

(12) United States Patent
Knap et al.

(10) Patent No.: US 8,642,305 B2
(45) Date of Patent: Feb. 4, 2014

(54) **BILE RESISTANT *BACILLUS* COMPOSITION SECRETING HIGH LEVELS OF PHYTASE**

(71) Applicant: Chr. Hansen A/S, Hørsholm (DK)

(72) Inventors: Inge Knap, Bettingen (CH); Ane Knarreborg, Lynge (DK); Thomas Dyrmann Leser, Frederiksberg C (DK); Bente Lund, Frederiksberg (DK)

(73) Assignee: Chr. Hansen A/S, Horsholm (DK)

( * ) Notice: Subject to any disclaimer, the term of this patent is extended or adjusted under 35 U.S.C. 154(b) by 0 days.

(21) Appl. No.: 13/676,879

(22) Filed: Nov. 14, 2012

(65) Prior Publication Data

US 2013/0071907 A1   Mar. 21, 2013

Related U.S. Application Data

(62) Division of application No. 12/667,215, filed as application No. PCT/EP2008/057296 on Jun. 11, 2008, now Pat. No. 8,334,123.

(30) Foreign Application Priority Data

Jul. 6, 2007   (EP) ..................................... 07111939

(51) Int. Cl.
*C12P 1/04*   (2006.01)
(52) U.S. Cl.
USPC ...................... 435/170; 424/93.462
(58) Field of Classification Search
USPC .............................. 435/170; 424/93.462, 170
See application file for complete search history.

(56) References Cited

U.S. PATENT DOCUMENTS

| 6,255,098 B1 | 7/2001 | Oh et al. | |
| 2003/0124104 A1* | 7/2003 | Farmer ........................ | 424/93.46 |

FOREIGN PATENT DOCUMENTS

| WO | WO-97/33976 | 9/1997 |
| WO | WO-03/039260 A2 | 5/2003 |
| WO | WO-2004/015084 A2 | 2/2004 |
| WO | WO-2004/080200 A1 | 9/2004 |

OTHER PUBLICATIONS

Annex to EPO Form 2004, Communication Pursuant to Rule 71(3) EPC European Patent Application No. 07 111 939.0 dated Dec. 30, 2011.
Carvalho N. Hansen S: "Prospects for probiotics in broilers" Feed International, [Online] vol. 26, No. 10, Nov. 2005, http://www.stocarstvo.com/ishrana/probiotics_in_broilers.html [retrieved on Dec. 10, 2007].
Chr. Hansen A/S: GalliPro [Online], http://www.chr-hansen.com/gallipro.html[retrieved on Oct. 12, 2007].
Communication Pursuant to Article 94(3) EPC EP 07 111 939.0 dated Apr. 20, 2011.
European Patent EP 07111939.0—Communication dated Aug. 12, 2011, regarding A94(3) communication dated Apr. 20, 2011.
G. Cenci et al., "Tolerance to challenges miming gastrointestinal transit by spores and vegetative cells of *Bacillus clausii*", Journal of Applied Microbiology 101 (2006) pp. 1208-1215.
Huynh A. Hong et al., "The use of bacterial spore formers as probiotics", FEMS Microbiology Reviews 29, (2005) 813-835.
M.E. Sanders et al., "Sporeformers as Human Probiotics: *Bacillus, Sporolactobacillus,* and *Bredibacillus*", Institute of Food Technologists, vol. 2, 2003—Comprehensive Reviews in Food Science and Safety, pp. 101-110.
Non-Final Office Action U.S. Appl. No. 12/667,215 dated Nov. 1, 2011.
Non-final Office Action U.S. Appl. No. 12/667,215 dated Sep. 9, 2011.
Xiaohua Guo et al., "Screening of *Bacillus* strains as potential probiotics and subsequent confirmation of the in vivo effectiveness of *Bacillus subtilis* MA139 in pigs", Antonie Van Leeuwenhoek. (2006) 90 pp. 139-146.
XP-002461912—Database WPI Week 200369 Derwent Publications Ltd., London, GB; AN 2003-728064 & KR 2002 025 395 A (Bionet Co Ltd) Apr. 4, 2002.

\* cited by examiner

*Primary Examiner* — Ruth Davis
(74) *Attorney, Agent, or Firm* — Foley & Lardner LLP

(57) ABSTRACT

A *bacillus* composition characterized by fast germination and outgrowth in bile salts (simulated gut environment) and by high-level secretion of phytase. The *bacillus* composition may be used as supplement in animal feed where it has a probiotic (health promoting) effect and increases the digestion and availability of nutrients from animal feeds.

7 Claims, 2 Drawing Sheets

Figure 1: *B.subtilis* strains

Figure 1:
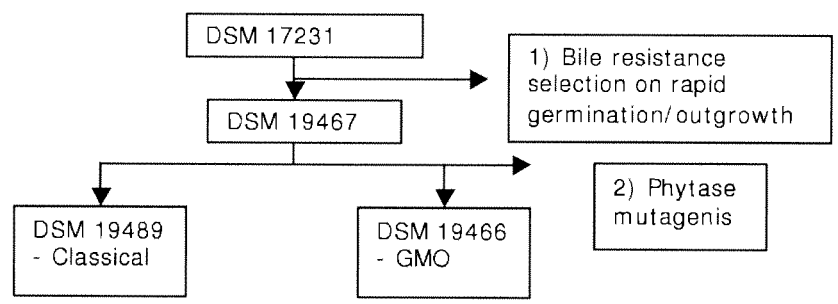

Figure 2 A and 2 B
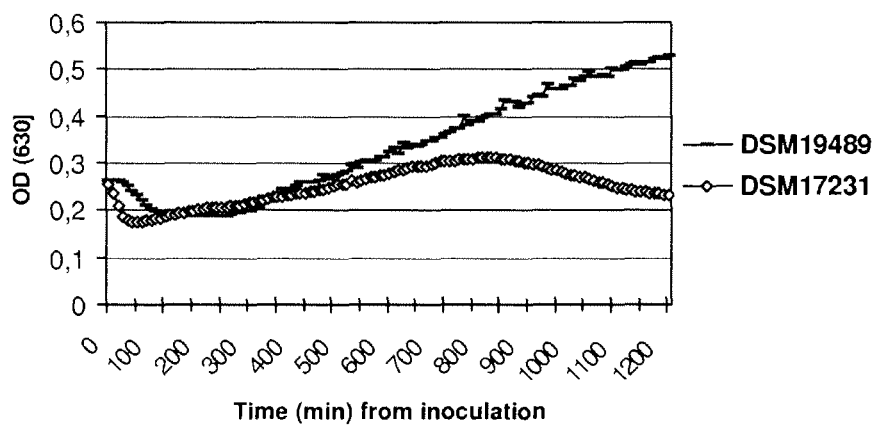
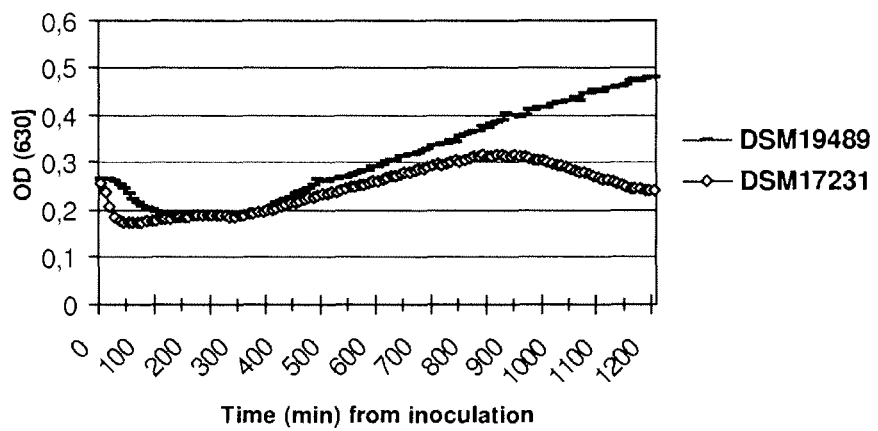
Figure 2A (4mM) and 2B (6mM). Time (min) from $10^8$ spores/ml until OD 0.4 $_{630}$ is reached

BILE RESISTANT BACILLUS COMPOSITION SECRETING HIGH LEVELS OF PHYTASE

CROSS REFERENCE TO RELATED APPLICATIONS

This application is a divisional of U.S. application Ser. No. 12/667,215, filed May 26, 2010, which is a National Phase of PCT/EP2008/057296, filed Jun. 11, 2008, which claims benefit of EP 07111939.0, filed Jun. 7, 2007, each of which is incorporated by reference in its entirety.

FIELD OF THE INVENTION

The present invention relates to a *bacillus* composition characterized by fast germination and outgrowth in bile salts (simulated gut environment) and by high-level secretion of phytase. The *bacillus* composition may be used as supplement in animal feed where it has a probiotic (health and growth promoting) effect and increases the digestion and availability of nutrients from animal feeds.

BACKGROUND ART

Probiotic bacteria such as *Bacillus subtilis* and *Bacillus licheniformis* are used in the animal feed industry as supplement to the diet. Their usage is related to the ability of *bacillus* to replace or reduce the use of antibiotics, which are used as growth promoters in the animal feed industry.

Christian Hansen A/S, Denmark commercializes an example of such a probiotic growth-promoting product under the trade name GalliPro® (deposited as DSM 17231). GalliPro® is a *Bacillus subtilis* spore cell composition.

Besides the suggested mode of actions (e.g. immune modulation, gut flora modifier) probiotic *bacillus* are able to produce many beneficial components, such as enzymes, which are excreted in the gastro intestinal tract (GIT) when used as animal feed supplement. Enzymes such as phytase are excreted and improve the digestion and better uptake of animal feed (higher digestibility). The diet (feed) is mostly composed of plant origin such as grains, corn, soybean, soy oil and amino acids. Overall these effects contribute to the production of cost effective animal products.

One of the widely used enzymes in the animal feed industry is phytase. Phytase is applied for improving the digestibility of phosphorous in animal diets. Phytate is the pre-dominant form of phosphorus in cereal grains, oilseeds and legumes. However, monogastric animals, such as pigs, poultry and fish, utilize this source of phosphate poorly because they lack the requisite gastrointestinal tract enzyme for release of the phosphate from the organic complex of phytate. Consequently, a large proportion of phytate in the feed consumed is passed through the GI-tract and excreted in the manure. In soil and water environments the catalyzed release of phosphate occurs, and phytate in manure poses a serious phosphorus pollution problem contributing to the eutrophication of surface waters. In addition, producers have to use expensive supplementary feed phosphorus to meet animals' dietary requirements. Further, phytate has anti-nutritive properties including formation of complexes with proteins and divalent cat ions, thus reducing their bioavailability.

It has been well documented that phytase supplementation improves phosphate use in monogastric production animals, and has a positive effect on the bioavailability of minerals.

*Bacillus* spores can pass the acidic gastric barrier and germinate and outgrow within the gastrointestinal (GIT) of the animals. This has great advantages, since when ingested they can excrete numerous types of beneficial components, e.g. bacteriocins and also excrete useful enzymes such as phytase. Moreover, the *bacillus* spores are thermostabile during a feed pelletizing process and are thereby an excellent delivery system to get both bacteriocins and enzymes into the GIT.

In the survival and proliferation process of *bacillus* in GIT, the role of bile is important. Bile is produced in the liver and stored in the gallbladder. Bile contains water, lecithin, bilirubin and biliverdin and bile salts.

It is known from the literature that bile has some negative influences on the survival and germination and outgrowth of *bacillus* spore cells to vegetative cells in the GIT of animals. Therefore research is ongoing to find probiotic bile resistant *Bacillus* strains.

The article (Antonie Van Leeuwenhoek. 2006 August; 90(2): 139-46. Epub 2006 Jul. 4) describes isolation of a number of *Bacillus* samples/cell directly from the intestine of chickens. The isolated *bacillus* cells were tested for probiotic activity. The six bacilli with highest probiotic activity were testes for bile salt resistance and it was found that a specific highly probiotic *bacillus* has a relatively high level of bile salt resistance. In this article there is no special focus on any time periods for the testing of bile resistance. In the experimental part the *bacillus* spore cells are simply tested for resistance after 5 days of presence in bile salt (see paragraph "Simulated small intestinal fluid tolerance test" on page 141).

US2003/0124104A describes that probiotic conventional *bacillus* endospores are sensitive to low concentration of bile salts, i.e. spore germination and/or rehydration is inhibited by the presence of even low concentrations of bile salts. This is contrary to other bacteria such as enteric pathogens, such as *E. coli* or *S. aureus* (see section [0014] to [0015]). In view of this it is suggested to screen/select for *bacillus* spores that are resistant to the inhibitory activity of bile salts, and as a result, germinate into vegetative cells, which then colonize the colon (see [0019]).

The working examples are all in presence and no real experimental data of actually screened specific *Bacillus* cell are provided in the description. Further the bile salt screening conditions are relatively generically described. In particular there are no indications of any time periods for the selections of bile resistance. Said in other words, based on the only broad/generic teaching of this document one may select *Bacillus* cells that only can outgrow (germinate) slowly, i.e. are capable of germinating from spores to vegetative cells after e.g. 20 hours in presence of relevant amount of bile salt.

In this document there is no description or suggestion to select for *bacillus* cells that can outgrow (germinate) rapidly, i.e. capable of germinating and outgrowing from spores to vegetative cells reaching a defined growth point within a certain time interval in presence of a relevant amount of bile salt.

In summary, the prior art references relating to selection/screening of bile resistant *bacillus* cells are not focusing on rapid outgrowth/germination from spore cells to vegetative *bacillus* cells.

The prior art describes a number of tests/screening systems for selection of *bacillus* strains producing phytase enzymes.

An example is U.S. Pat. No. 6,255,098 in which *bacillus* strains producing phytase enzymes are identified. Nothing is mentioned about bile resistance of the identified *bacillus* strains.

SUMMARY OF THE INVENTION

The problem to be solved by the present invention is to provide a *bacillus* composition which excretes high amounts of phytase in the gastro intestinal tract (GIT) of an animal.

The solution is based on that the present inventors have developed a novel selection method for the identification of new improved *bacillus* compositions.

A novel important step of the herein described new selection method is to specifically screen/select for *bacillus* spore cells with improved/rapid speed of germination and outgrowth from spores to vegetative cells in the presence of bile salts.

As described above, the prior art has described methods for selecting *bacillus* cells capable of growing in presence of bile salts, but the prior art screening/selection methods do NOT focus on the speed of germination and outgrowth in the presence of bile salt. Accordingly, the prior art selected bile resistant *bacillus* cells do not germinate and grow fast enough to comply with the speed of germination and outgrowth criteria as described herein. For instance, *bacillus* cells isolated directly from the intestine of e.g. chickens (as e.g. described in the Antonie Van Leeuwenhoek article discussed above) in the gut environment are not selected (under natural pressure) to germinate and outgrow rapidly in the intestine.

As shown in working examples herein this is also true for the commercial available *Bacillus* composition GalliPro®, which simply germinates and outgrows too slowly and does not reach the defined growth point within the first 20 hours in presence of physiological levels of bile salts to comply with the speed of germination and out-growth criteria as described herein. GalliPro® is a *Bacillus subtilis* composition that is commercially successful.

The herein described novel DSM 19467 was selected by using GalliPro® as a starting strain and a selective pressure method and a subsequent isolation for rapid germination and outgrowth from spores to vegetative cells in presence of bile salt as described herein.

See e.g. table 1 for further details (GalliPro® may herein also be termed DSM 17231). In FIG. 1 herein this is illustrated schematically.

In summary, it is believed that no prior art describes an isolated *Bacillus* composition, which comprises from $10^5$ to $10^{12}$ CFU/g *bacillus* cells, wherein the cells of the *bacillus* composition complies with the rapid germination and outgrowth in the presence of bile salt criteria as described herein.

Without being limited to theory, the present inventors have identified that rapid germination and outgrowth is a very important aspect of the invention as *bacillus* spores, which are resistant to bile but do not germinate and outgrow fast enough, will be excreted before any positive characteristics, such as phytase production, can be made in significant amounts by the vegetative *bacillus* cells.

*Bacillus* spores germinating too slowly will simply pass through the gastro intestinal tract (GIT) before the bacteria can produce any significant amount of e.g. phytase.

After a number of detailed tests and analysis, the inventors therefore chose to work with a time range up to 20 hours and select the fastest germinating and outgrowing spores within this time period in presence of high physiological concentrations of bile salts. Without being limited to theory and based on the herein disclosed detailed experimental work, the present inventors have identified that it is important to have a rapid germination and outgrowth within the first 18 and 19 hours in the presence of 4 and 6 mM bile salt, respectively.

The present inventors then identified that once *bacillus* cells, with rapid germination and outgrowth in bile salt medium, have been selected these cells are highly useful as starting cells for mutagenesis to obtain new cells with improved phytase production.

As show in FIG. 1 and table 2, the rapid outgrowing bile resistant selected strain, DSM 19467, was used as starting strain for classical mutation and the high phytase producing DSM 19489 strain was selected. Similarly a Genetic Modified Organism (GMO) DSM 19466 strain was made by using DSM 19467 as starting strain. As can be seen in table 2 and the related description of example 4, DSM 19489 and DSM 19466 produce significantly more phytase than DSM 19467 and GalliPro®. The high phytase producing DSM 19489 and DSM 19466 strains were re-checked for their ability to germinate and outgrow fast as described herein and they had maintained the rapid germination and outgrowth of the rapid outgrowing bile resistant selected strain DSM 19467 (see example 5 herein).

In FIG. 1 herein this is illustrated schematically.

The herein described novel probiotic *bacillus* cells are thus the ones, which are bile resistant, germinating and outgrowing fast, and excreting high amounts of phytase. The obtained strains are extremely useful as probiotic *bacillus* compositions for the addition to animal feed. It combines all the beneficial abilities of the probiotic bacteria to survive and proliferate in the gut of animals (with high levels of bile salt present), inhibit pathogenic bacteria (production of bacteriocins), and additionally excrete high amounts of phytase beneficial and useful for the digestion and uptake of phosphorous available from phytate.

Accordingly, a first aspect of the invention relates to a *bacillus* composition, which comprises from $10^5$ to $10^{12}$ CFU/g *bacillus* spore cells, wherein the *bacillus* composition is characterized by:

(i): the *bacillus* spores have a rapid germination and outgrowth from spore to vegetative cell in presence of a bile salt medium comprising 4 and 6 mM bile salts, defined by that the *bacillus* spores reach a vegetative cell growth point of 0.4 $OD_{630}$ within less than 18 and 19 hours, respectively, wherein the vegetative cell growth point is the point in the growth curve where the OD value starts to increase (due to growth of the vegetative cells) in a continuous way and reaches an $OD_{630}$ of 0.4;

(I): wherein the bile salt medium is the standard known non-selective Veal Infusion Broth (VIB) medium of example 1 herein supplemented with a bile salt mixture comprising the conjugated bile salts taurodeoxycholate and glycodeoxycholate and the deconjugated bile salt deoxycholate in the proportions 60% of the taurodeoxycholate, 30% of the glycodeoxycholate and 10% of deoxycholate; and wherein the OD assay analysis is performed by the following steps:

(a): filling a well in a microtiter plate with 0.150 ml bile salt medium having $10^8$ *bacillus* spores per ml medium (i.e. this is time zero); and (b): incubating the plate at 37° C. under atmospheric conditions and measuring the $OD_{630}$ values, using a spectrophotometer and with agitation before each reading, to get a representative growth curve over time;

and (ii) the *bacillus* vegetative cells are producing phytase in an amount of at least 1.25 times more than the reference *bacillus* cell DSM 19467, wherein the produced phytase amount is measured by the standard phytase assay of example 2 herein after 4 hours growth at 37° C. in the standard known non-selective Heart Infusion Broth (HIB) medium of example 2 herein; and wherein the phytase assay analysis is performed by the following steps:

(a): making an overnight culture of *bacillus* vegetative cells in an enriched culture medium; and (b): transferring a 1% inoculum from the overnight culture to HIB medium (i.e. this is time zero) and incubation at 37° C. until phytase activity measurement.

As discussed above, the reference *bacillus* cell DSM 19467 is selected for rapid germination and outgrowth in presence of bile salt by using GalliPro® as starting strain. DSM 19467 is not selected for improved phytase production. Without being limited to theory, it is believed that the herein relevant phytase production of DSM 19467 corresponds to GalliPro®.

In relation to point (i) the vegetative cell growth point for GalliPro is at least 20 hours after incubation in 4 and 6 mM bile salt and for the novel DSM 19489 strain, as described herein, it is after 14 and 15 hours in 4 and 6 mM bile salts, respectively (see FIG. 2 and working example 3 herein).

It is here relevant to note that the present inventors also tested the commercial available product CALSPORIN® (Calpis Co., Ltd., Japan) to determine the vegetative cell growth point under the conditions of point (i) of first aspect. As for GalliPro® the commercial product CALSPORIN® is a *Bacillus subtilis* composition used as a probiotic feed additive. The vegetative cell growth point under the conditions of point (i) of first aspect for CALSPORIN® was more than 20 hours at 4 and 6 mM bile salts, respectively. This is considerably more than the 18 and 19 hours required under point (i) and this illustrates that commercially available products have hitherto not been selected for rapid germination and outgrowth. As discussed above, "natural" bacillus cells have not been under any selective pressure to get rapid germination and outgrowth. Without being limited to theory, it is therefore believed that "natural" *bacillus* cells are not complying with the conditions of point (i) of first aspect.

Both the bile resistance [of point (i)] and phytase assay [of point (ii)] are based on known, commercially available standard elements (such as e.g. standard media, bile salts; standard OD measurements and standard tests).

The reference *bacillus* cell is deposited as DSM 19467 and is therefore publicly available.

The *Bacillus subtilis* cell GalliPro® is deposited as DSM 17231 (named "GalliPro®") and is therefore publicly available.

Accordingly, based on the detailed assay description herein (see e.g. example 1 herein for bile resistance assay and example 2 herein for phytase assay) the skilled person is routinely able to repeat these assays to objectively determine whether a specific *bacillus* cell of interest complies with the bile resistance [of point (i)] and phytase [of point (ii)] levels of the first aspect of the invention.

The novel *bacillus* composition as described herein may be used as a probiotic supplement to animal feed. The dose and administration may be done according to the art as for instance as done for prior art GalliPro® *bacillus* compositions.

Accordingly, a second aspect of the invention relates to a method for feeding an animal comprising administering the *bacillus* composition of first aspect and herein described related embodiments to an animal in conjunction with other animal feed ingredients.

A third aspect of the invention relates to a method for screening and isolating a novel *bacillus* cell comprising the following steps:

(a): selecting and isolating from a pool of individual *bacillus* spore cells of a new *bacillus* spore cell that is capable of germinating and outgrowing so rapidly that it reaches a vegetative cell growth point within less than 18 and 19 hours under the conditions of point (i) of first aspect;

(b): making a vegetative *bacillus* cell from the isolated spore cell of step (a) and mutating the novel selected and isolated cell to get a pool of new individual *bacillus* vegetative cells;

(c): selecting and isolating from the pool of new individual *bacillus* vegetative cells of step (b) a new *bacillus* vegetative cell that is capable of producing phytase in an amount of at least 1.25 times more than the reference *bacillus* cell deposited as DSM registration number 19467 under the conditions of point (ii) of first aspect; and (d): analyzing the high producing vegetative *bacillus* cell of step (c) to confirm that it has maintained the rapid germination and outgrowth of step (a) and isolating the selected *bacillus* cell.

It is evident to the skilled person that once the inventors herein have disclosed the relevant test assays (in particular the assay for testing rapid germination and out-growth of example 1) plus the reference strain DSM 19467 it will be routine work for the skilled person to select other new *bacillus* cells complying with the criteria of the first aspect herein.

As discussed herein, by using the novel screening/selection method as described herein the inventors have selected and isolated a number of new improved *bacillus* cells, which have been deposited.

Accordingly, a fourth aspect of the invention relates to a *bacillus* cell selected from the group consisting of:

(a) a *Bacillus subtilis* cell with registration number DSM 19467;

(b) a *Bacillus subtilis* cell with registration number DSM 19489; and (c) a *Bacillus subtilis* cell with registration number DSM 19466;

or a mutant strain thereof, wherein the mutant strain is obtained by using one of the deposited strains as starting material and wherein the mutant strain retains the essential properties of the deposited strain.

Embodiment of the present invention is described below, by way of examples only.

DEFINITIONS

All definitions of herein relevant terms are in accordance of what would be understood by the skilled person in relation to the herein relevant technical context.

The term "*bacillus* cell" relates herein to both a bacillus spore cell and a *bacillus* vegetative cell.

The term "*bacillus* spore" in relation to *bacillus* spore cell relates herein to a spore that according to the art may be characterized as a dormant, tough, non-reproductive structure produced by *bacillus* bacteria. The primary function of spores is generally to ensure the survival of a bacterium through periods of environmental stress. They are therefore resistant to ultraviolet and gamma radiation, desiccation, lysozyme, temperature, starvation, and chemical disinfectants. Spores are commonly found in soil and water, where they may survive for long periods of time. The spore coat is impermeable to many toxic molecules and may also contain enzymes that are involved in germination. The core has normal cell structures, such as DNA and ribosomes, but is metabolically inactive. When a bacterium detects that environmental conditions are becoming unfavorable it may start the process of sporulation, which takes about eight hours.

The term "*bacillus* vegetative cell" relates to functional vegetative *bacillus* cells, which can divide to produce more vegetative cells.

The term "germination and outgrowth" relates to that bacillus spores germinate and outgrow to bacillus vegetative cells. As know to the skilled person reactivation of the spore occurs when conditions are favorable and involves germination and outgrowth. Germination involves the dormant spore starting metabolic activity and thus breaking hibernation. It is commonly characterized by rupture or absorption of the spore coat, swelling of the spore, an increase in metabolic activity, and loss of resistance to environmental stress. Outgrowth follows germination and involves the core of the spore manufacturing new chemical components and exiting the old spore coat to develop into a functional vegetative bacterial cell, which can divide to produce more cells. Growth curves (OD versus time) of bacillus cells show distinct growth phases. As the spores are transferred to a nutrient rich medium the germination is initiated followed by a temporary decrease in OD (phase I), which is due to the release of dipicolinic acid and consequently hydration of the spore coat. In the second phase (phase II=out-growth phase) there is a period with a relative little change in OD, until the spores are developed into a functional vegetative bacterial cells, which can divide to produce more cells and thereby give a continuous increase in OD value. The point when one starts to get the continuous increase in OD values reaching an OD of 0.4 is herein termed "vegetative cell growth point".

The term "optical density" is defined as a measure of optical absorbance using a spectrophotometer. Optical density (OD) is the absorbance of an optical element for a given wavelength λ per unit distance. If OD is e.g. measured at wavelength 630 nm it may be referred to as $OD_{630}$.

DRAWINGS

FIG. 1: In this figure the steps to get to the herein novel improved strains are illustrated. The working examples herein were started from DSM 17231 (GalliPro®), which was classically mutated and screened/selected for rapid germination and outgrowth in presence of bile salt to get the novel selected strain DSM 19467. DSM 19467 was used as starting strain for classical mutation and the high phytase producing DSM 19489 strain was selected. Similarly a Genetic Modified Organism (GMO) DSM 19466 strain was made by using DSM 19467 as starting strain.

FIGS. 2a and 2b: These figures show clearly the improved rapid germination and out-growth of DSM 19489 bacillus spores of the present invention as compared to DSM 17231 in presence of 4 and 6 mM bile salt as described herein.

DETAILED DESCRIPTION OF THE INVENTION

Bacillus Composition:

The term "bacillus composition" shall be understood according to the art. It is herein understood as a bacillus composition comprising a number of bacillus spore cells with a characteristic of interest.

The bacillus composition may comprise different types of bacillus cells (e.g. B. subtilis and Bacillus licheniformis). In essence the composition shall simply comprise the amount of bacillus spore cells given in the first aspect herein, wherein the bacillus cells comply with the criteria given in the first aspect.

As known to the skilled person, herein commercially relevant bacillus spore cell compositions are generally made by fermentation. The obtained spore cells are generally concentrated, dried, mixed with a carrier and packed into a suitable container.

The relevant e.g. $10^5$ to $10^{12}$ CFU/g bacillus cells of the composition may be present in a commercially relevant form known to the skilled person.

Accordingly, in an embodiment $10^5$ to $10^{12}$ CFU/g bacillus spore cells of the composition are present as dried (e.g. spray dried) cells or as frozen spore cells.

In a preferred embodiment the bacillus composition comprises from $10^6$ to $10^{12}$ CFU/g bacillus spore cells, more preferably from $10^2$ to $10^{12}$ CFU/g bacillus spore cells. The term "CFU/g" relates to the gram weight of the composition as such, including suitable relevant additives present in the composition. It does not include the weight of a suitable container used to package the bacillus composition.

An embodiment relates to that the bacillus composition is packaged into a suitable container.

As known to the skilled person a commercially relevant bacterial composition generally also comprises other relevant additives such as e.g. one carrier/ingredient of the group belonging to whey, whey permeate, calcium carbonate/limestone and anti caking agents such as aluminum silicates and kieselgur (diatomaceous earth).

Beside the herein relevant bacillus cells the composition may also comprise other relevant microorganisms of interest such as e.g. lactic acid bacteria of interest.

Bacillus Cell

The bacillus cell may be any relevant bacillus cell of interest.

In a preferred embodiment the bacillus cell is at least one bacillus cell selected from a bacillus species selected from the group consisting of:

Bacillus subtilis, Bacillus uniflagellatus, Bacillus lateropsorus, Bacillus laterosporus BOD, Bacillus megaterium, Bacillus polymyxa, Bacillus licheniformis, Bacillus pumilus, and Bacillus sterothermophilus, Bacillus coagulans, Bacillus thermophilus, Bacillus mycoides, Bacillus cereus, and Bacillus circulans.

In a more preferred embodiment the bacillus cell is a B. subtilis cell or a Bacillus licheniformis cell.

The most preferred is wherein the bacillus cell is a B. subtilis cell.

Assay to Select for Rapid Germination and Outgrowth in the Presence of Bile Salt As discussed above the bile resistance assay of point (i) of first aspect is based on known commercially available standard elements (such as e.g. standard media, bile salts; standard OD measurements).

Accordingly, based on the detailed assay description herein (see e.g. example 1 herein) the skilled person is routinely able to repeat this assay to objectively determine whether a specific bacillus spore cell of interest complies with the rapid germination and outgrowth from spore to vegetative cell criteria as described in point (i).

In point (i) it is explained that vegetative cell growth point is the point in a growth curve starting with $10^8$ spores/ml corresponding to OD of around 0.2-0.3 until the time where the OD value has increased (due to growth of the vegetative cells) in a continuous way and has reached OD 0.4. This is in accordance with how a skilled person would understand such a vegetative cell growth point and based on a growth curve the skilled person may routinely determine this, within a limited variability of around ±30 minutes, as explained herein.

Working example 1 herein provides a detailed description of a bile resistance assay suitable to select for rapid germination and outgrowth in the presence of bile salt. The detailed conditions of this example 1 is herein a preferred assay to determine if a bacillus spore cell of interest complies with the criteria of point (i) of first aspect.

The term "bile salt" relates to the salt of bile acids. Bile acids are steroid acids found predominantly in the bile of mammals. They are produced in the liver by the oxidation of cholesterol, and are stored in gallbladder and secreted into the intestine in the form of salts. They act as surfactants, emulsifying lipids and assisting with their absorption and digestion. The bile salts used in example 1 were prepared mimicking the physiological concentrations and compositions of porcine bile salts. As known to the skilled person porcine bile salts compositions may herein be considered as relatively "harsh" conditions as compared to avian bile salt compositions.

The term "bile salt medium" relates to a medium comprising relevant *bacillus* growth ingredients such as relevant nutrients and bile salt.

Vegetative Cell Growth Point—in Bile Salt Assay—Point (i) of First Aspect

As said above, in relation to point (i) of first aspect the *bacillus* spore cells, as described herein, have a germination and outgrowth from spore to vegetative cell that is so rapid that they reach a vegetative cell growth point of 0.4 OD within less than 18 and 19 hours at 4 and 6 mM bile salts, respectively.

As said above, the novel DSM 19467 strain reaches the vegetative cell growth point after 14 and 15 hours incubation in 4 and 6 mM bile salt, respectively.

Accordingly, in a preferred embodiment the *bacillus* spores reach the vegetative cell growth point after 17 and 18 hours incubation in 4 and 6 mM bile salt under the conditions of point (i) of first aspect, more preferably the *bacillus* spores reach the vegetative cell growth point after 15 and 16 hours incubation in 4 and 6 mM bile salt under the conditions of point (i) of first aspect.

As explained above and shown schematically in FIG. 1 the herein described novel DSM 19467 strain was selected by using the commercially available GalliPro® as a starting strain for mutagenesis and selection for rapid outgrowth in presence of bile salt as described herein.

GalliPro® is a composition comprising *Bacillus subtilis* cells and the *Bacillus subtilis* is deposited as DSM 17231. Accordingly, GalliPro® may herein be seen as a reference strain.

As said above, the vegetative cell growth starting point for GalliPro is after 20 hours incubation in 4 and 6 mM bile salts under the conditions of point (i) of first aspect. Accordingly, in an embodiment the *bacillus* spores reach the vegetative cell growth point at least 3 hours earlier than the reference *Bacillus subtilis* spores cells deposited as DSM 17231 ("GalliPro®") under the conditions of point (I) of first aspect, more preferably the *bacillus* spores reach the vegetative cell growth point at least 4 hours earlier than the reference *Bacillus subtilis* spores cells deposited as DSM 17231 ("GalliPro®") under the conditions of point (i) of first aspect, and most preferably the *bacillus* spores reach the vegetative cell growth starting point at least 5 hours earlier than the reference *Bacillus subtilis* spores cells deposited as DSM 17231 ("GalliPro®") under the conditions of point (i) of first aspect.

Phytase Assay

As discussed above the phytase assay of point (ii) of first aspect is based on standard known commercially available elements (such as e.g. standard media, standard test).

Accordingly, based on the detailed assay description herein (see e.g. example 2 herein) the skilled person is routinely able to repeat this assay to objectively determine whether a specific *bacillus* vegetative cell of interest complies with the produced phytase amount as described in point (ii).

Working example 2 herein provides a detailed description of a phytase assay. The detailed conditions of this example 2 are herein a preferred phytase assay to determine if a *bacillus* vegetative cell of interest complies with the criteria of point (ii) of first aspect.

Produced Amount of Phytase—Point (ii) of First Aspect

As said above, in relation to point (ii) of first aspect, the *Bacillus* vegetative cells are producing phytase in an amount of at least 1.25 times more than the reference *Bacillus* cell DSM 19467 under the conditions of point (ii) of first aspect.

In a preferred embodiment, the *Bacillus* vegetative cells are producing phytase in an amount of at least 1.5 times more than the reference *Bacillus* cell DSM 19467 under the conditions of point (ii) of first aspect, more preferably the *Bacillus* vegetative cells are producing phytase in an amount of at least 1.75 times more than the reference *Bacillus* cell DSM 19467 under the conditions of point (ii) of first aspect.

A Method for Feeding/Administering *Bacillus* Spores to an Animal

As said above a second aspect of the invention relates to a method for feeding an animal comprising administering the *bacillus* composition of first aspect and herein described related embodiments to an animal in conjunction with other animal feed ingredients.

The animal may be any animal of interest. Preferably, the animal is an animal selected from the group consisting of poultry, ruminants, calves, pigs, rabbits, horses, fish and pets.

When administering GalliPro® according to the art it is normally done in a dose from around $10^4$-$10^8$ CFU/g feed, commonly $10^5$-$10^6$ CFU/g feed or in doses equivalent to normal feed intake/kg live weight animal.

Alternatively the *bacillus* spores may be administered to the animal in one of the following ways:
(1): put it into drinking water for animals;
(2): sprayed onto animals; or
(3): application via paste, gel or bolus.

A Method for Screening and Isolating a Novel *bacillus* Cell

As said above, the third aspect relates to a method for screening and isolating a novel *bacillus* cell.

In the method of the third aspect is selected for a *bacillus* cell capable of fulfilling the conditions of point (i) and (ii) of the first aspect.

As understood by the skilled person, the specific herein detailed described bile resistance and phytase amount assay (see e.g. example 1 herein for bile resistance assay and example 2 herein for phytase assay) parameters may be changed to make a alternative screening method that still obtains the main goals as described herein, i.e. a *bacillus* cell that is capable of fulfilling the conditions of point (i) and (ii) of the first aspect.

In a preferred embodiment, bile resistance assay of example 1 is used in step (a) of the screening method of third aspect and the phytase assay of example 2 is used in step (c) of the screening method of third aspect.

In step (d) of the screening method of third aspect a vegetative *bacillus* cell is isolated. This vegetative *bacillus* cell may be used to make *bacillus* spores from.

Accordingly, in an embodiment the screening method of third aspect is followed by a extra step (e), wherein the isolated *bacillus* vegetative cell of step (d) is fermented to make from $10^5$ to $10^{12}$ *bacillus* vegetative cells and these $10^5$ to $10^{12}$ *bacillus* vegetative cells are used to make $10^5$ to $10^{12}$ *bacillus* spore cells, which are isolated to give a *Bacillus* composition, which comprises from $10^5$ to $10^{12}$ CFU/g *bacillus* spore cells.

The end result of step (e) is a novel *Bacillus* composition, which comprises from $10^5$ to $10^{12}$ CFU/g *bacillus* spore cells, and wherein the *bacillus* cells are capable of fulfilling the conditions of point (i) and (ii) of the first aspect.

Accordingly, a separate aspect of the invention relates to a *Bacillus* composition, which comprises from $10^5$ to $10^{12}$ CFU/g *bacillus* spore cells, and wherein the *bacillus* cells are capable of fulfilling the conditions of point (i) and (ii) of the first aspect obtainable by the screening method of third aspect followed by extra step (f) described above.

In step (b) of the screening method of third aspect is made mutations of the earlier selected bile resistant *bacillus* cell to select for high phytase producing cells in step (c). As understood by the skilled person this may e.g. by classical mutation (e.g. by chemical treatments or UV) of specific exchange of genes to make a so-called Genetic Modified Organism (GMO).

For instance, the herein described novel GMO strain DSM 19466 was derived from GalliPro® and was first made bile resistant as described in the working example herein to obtain DSM 19467. Thereafter, the promoter of phytase in the strain DSM 19467 was exchanged with another *bacillus* promoter to make it a high producer of phytase enzyme and thus DSM 19466 was obtained.

Similar, the novel high phytase producing strain DSM 19489 was obtained by using classical mutation starting from DSM 19467. See e.g. FIG. 1.

Deposited Strains

As said above a fourth aspect of the invention relates to a *bacillus* cell selected from the group consisting of:

(a) a *Bacillus subtilis* cell with registration number DSM 19467;

(b) a *Bacillus subtilis* cell with registration number DSM 19489; and (c) a *Bacillus subtilis* cell with registration number DSM 19466;

or a mutant strain thereof, wherein the mutant strain is obtained by using one of the deposited strains as starting material and wherein the mutant strain retains the essential properties of the deposited strain.

The fourth aspect of the invention relates to the herein described novel strain or "a mutant thereof".

It is clear for the skilled person that by using the deposited strain as starting material, the skilled reader can routinely, by conventional mutagenesis or re-isolation techniques, obtain further mutants or derivatives thereof that retain the herein described relevant features and advantages. Accordingly, the term "a mutant thereof" of the first aspect relates to mutant strains obtained by using the deposited strain as starting material.

This may alternatively be formulated as a method to obtain a strain, comprising using one of the herein deposited strain as starting strain, making mutants of the deposited strain and isolating a novel strain wherein the mutant has retained the essential properties of the deposited strain.

A sample of the novel *Bacillus subtilis* strain has been deposited at DSMZ (Deutsche Sammlung von Mikroorganismen und Zellkulturen GmbH, Maschroder Weg 1b, D-38124 Braunschweig) under the accession number DSM 19467 with a deposit date of Jun. 27, 2007. The deposit has been made under the conditions of the Budapest Treaty on the International Recognition of the Deposit of Microorganisms for the Purposes of Patent Procedure.

A sample of the novel *Bacillus subtilis* strain has been deposited at DSMZ (Deutsche Sammlung von Mikroorganismen und Zellkulturen GmbH, Maschroder Weg 1b, D-38124 Braunschweig) under the accession number DSM 19489 with a deposit date of Jun. 27, 2007. The deposit has been made under the conditions of the Budapest Treaty on the International Recognition of the Deposit of Microorganisms for the Purposes of Patent Procedure.

A sample of the novel *Bacillus subtilis* strain DSM 19466 has been deposited at DSMZ (Deutsche Sammlung von Mikroorganismen und Zellkulturen GmbH, Maschroder Weg 1b, D-38124 Braunschweig) under the accession number DSM 19466 with a deposit date of Jun. 27, 2007. The deposit has been made under the conditions of the Budapest Treaty on the International Recognition of the Deposit of Microorganisms for the Purposes of Patent Procedure.

EXAMPLES

Example 1

Bile Resistance Assay

Medium:

The medium was a standard non-selective commercial available medium Veal Infusion Broth (VIB) (Difco, 234420).

At the filing date of the present application the product catalogue ("Difco™/BBL™ Manual) from the provider BD Diagnostic Systems (www.bd.com) read in relation to the Veal Infusion Broth:

"Infusion from lean veal and peptone provide the nitrogen, vitamins, carbon and amino acids in veal infusion media. Sodium chloride maintains the osmotic balance of the formulations"; and The medium was prepared according to manufacture instructions by suspending 25 g of the Veal Infusion Broth powder in 1 L of purified water (2.5% solution) and heat with frequent agitation and boil for 1 minute to completely dissolve the powder. A 2.5% Veal Infusion Broth solution comprised per liter:

Lean Veal, Infusion: 10 g

Proteose Peptone: 10 g

Sodium Chloride 5 g

The medium was distributed into sterile bottles and autoclaved for 15 min at 121° C.

Bile Salt Solutions/Medium:

Mixtures of bile salts were prepared mimicking the physiological composition and concentration of bile salts in pig bile and the bile salts were dissolved in the Veal Infusion Broth medium as prepared above to give a final bile salt concentration of 8 mM. The conjugated bile salts were taurodeoxycholate (Sigma T-0875, U.S.) and glycode-oxycholate (Sigma G-9910, U.S.) and the deconjugated bile salt deoxycholate (Sigma D-5670 U.S.) and the final 8 mM mixed bile salt solution contained 60% of the tauro-deoxycholate, 30% of the glycodeoxycholate and 10% of deoxycholate.

Before autoclaving for 15 minutes at 121° C., the solutions were adjusted to pH 7.4 using sodium hydroxide. The prepared 8 mM bile salt medium, were diluted to get bile salt concentrations of 0, 1, 2, 4, 6 and 8 mM.

The bile salts were added to the Veal Infusion Broth medium in a concentrated form. Accordingly, the final amount of lean veal infusion, Proteose Peptone and Sodium chloride were essentially as for the 2.5% Veal Infusion Broth medium before the bile salts were added.

Spore Suspensions

To distinguish between vegetative cells and spores and to ensure pure spore products for inoculation, the spore counts of the *bacillus* product were determined using +/− heat treatment at 80° C. for 10 min. After heat treatment and subsequent cooling to room temperature, serial 10-fold dilutions were conducted in saline peptone water. Duplicates of Tryptose Blood Agar plates (Difco 0232-01) were inoculated with 0.1 ml from the appropiate decimal dilutions. The plates were incubated at 37° C. until the next day. Based on preceding spore count determinations of the products, spore suspensions were prepared in sterile distilled water to reach final calculated spore concentration of $10^8$CFU/ml. The counts of vegetative cells and spores in the final inocula were determined using the method described above. The final concentration of $10^8$ CFU/ml corresponded to a start $OD_{630}$ at 0.2-0.3.

Growth Measurement: Optical Density Measurements

Sterile flat bottom 96 well microtiter plates were used (Greiner Bio-one GmbH, Germany). Each well was filled with 0.150 ml VIB inoculated with spores ($1\times10^8$ spores per ml equivalent/corresponding to a start $OD_{630}$~0.2-0.3) and the plates were incubated for 20 hours at 37° C. with a 1 minute shaking cycle of intensity 4 (high) before each reading.

To avoid condensation on the inside of the plate cover, the lids were exposed to a dilute solution of Triton X-100.

The germination and outgrowth kinetics of *Bacillus* strains were measured using a spectrophotometer at wavelength 630 nm ($OD_{530}$) (Bio-tek Instruments, Inc. VE). Readings were performed with 10 minute intervals and analyzed using the KC4™ software (Bio-tek Instruments, Inc., USA). After 20 h, data were exported to Excel® spreadsheets for further analysis, imported in SAS version 9.0 and statistically analyzed.

Example 2

Phytase Activity Assay

The method to measure and quantify the phytase enzyme units produced by the *bacillus* cells used in this study was adapted from Walsh et al. 2004, Biochemistry & Molecular Biology Education vol. 32 no 5 (336-340). Essentially, the only significant adaptation that was made in order to standardize the method for the purpose of growth kinetics, was by measuring phytase activity relative to the number of viable *Bacillus* cells using a spectrophotometer and measuring Optical Density (OD) at wavelength 600 diluting the cells 1:4 with dilution water if necessary. By using this method, one gets a relatively limited standard deviation.

Growth of *Bacillus* Cells

The *Bacillus* cells are inoculated and grown in a rich *Bacillus* growth medium at 37° C. and the growth of the *Bacillus* strains and the phytase activity followed at time intervals up to 24 hours.

The *bacillus* spores are propagated in Heart Infusion Broth (HIB) based media with the following composition:

| | |
|---|---|
| HIB (Bacto 238400) | 25 g/l |
| 0.5% Bacto yeast Extract (Difco 212750) | 5 g/l |
| 2 mM $CaCl_2$ (Merck 1.02382) | 0.294 g/l |

Autoclaved for 15 min at 121° C. and added sterile filtered 1% mannose and 1% Glucose HIB is a well-known commercially available non-selective medium. At the filing date of the present application the product catalogue from the provider BD Diagnostic Systems (www.bd.com) described that the composition/formula of Bacto™ Heart Infusion Broth per liter was:

| | |
|---|---|
| Beef Heart, Infusion from 500 g: | 10.0 g |
| Tryptose: | 10.0 g |
| Sodium Chloride: | 5.0 g |

The supplemented HIB is a medium with low phosphate content and is therefore suitable for phytase assays. After an overnight culture 1% inoculum is used in fresh HIB medium and incubation at 37° C. until activity measurement (for instance after 4, 6, 8 and 24 hours)

Incubation of the medium was done in either blue cap Nunc 50 ml or in smaller amounts (0.150 ml) in 96-well ELISA plates with good aeration.

Phytase Assay

The phytase assay is carried out on cell supernatants, since the enzyme is secreted to the media. The microtiter plates are centrifuged as 3600 RPM for 15 min. Larger volumes are centrifuged at 2400-3600 rpm for 15 min in an Eppendorf centrifuge. Carefully remove the supernatant, omitting cells before the phytase assay.

Solutions:

0.1 M TRIS/malate ph 7.0

Solution A: 0.1 M TRIS/malate (I-malic acid, Sigma M1000) pH 7.0+0.1 w/v Phytic acid sodium salt from corn (sigma P8810)+2 mM $CaCl_2$ (freshly prepared before assay)=substrate Solution B: 8 g Ammoniummolybdate (Sigma A7302)+50 ml $H_2O$+27 ml 10 M $H_2SO_4$+$H_2O$ ad 100 ml.

Solution C: 5 g $FeSo_4$ (sigma F 7002)+90 ml $H_2O$ (stirred until dissolved)+10 ml solution B (freshly made)

0.5 M TCA (Merck 1.00807.1000) 8% w/v 1 mM $KH_2PO_4$

The assay was performed in 96-well microtiter plate containing 0.020 ml of *Bacillus* supernatant wherein 0.080 ml of 0.1M Tris/Malic acid pH 7.0 buffer solution containing 0.1% Phytic acid and 2 mM $CaCl_2$ (Solution A) were added. The plate was incubated at 50° C. for 30 min (plate covered to avoid evaporation).

Color Reaction:

Add 0.100 ml 0.5 M Tri chloro-acetic acid TCA

Add 0.100 ml Fe++ solution (solution C)

Leave for 5 minutes at room temp. A blue color will appear.

Read absorbance at 600 nm.

This assay is measuring total free phosphate in the supernatant. In order to determine the background amount of free phosphate, the phytate assay also has to be performed without the presence of the substrate (phytic acid) for the phytase enzyme. This means that the Solution A in the assay (see above) is replaced with a simple TRIS/Malate buffer pH 7.0.

Calculation of Phytase Activity

The absorbance measured in the assay will represent both the free phosphate in the medium and the phosphate released from the phytase activity and therefore the free phosphate in the medium needs to be subtracted. To do this, the sample is measured in a buffer with and without phytic acid, and the two are subtracted, to get pure phytase activity. Corrected for cell density ($OD_{600}$) the phytase activity of the *Bacillus* culture is expressed as the activity (units absorbance) as has been done in this case:

$$\frac{\text{Sample with buffer} + \text{phytic acid sample and buffer} - \text{phytic acid}}{OD \text{ measure before centrifugation}}$$

Example 3

Selection of Bile Resistant *Bacillus subtilis* cell DSM 19467

The starting *bacillus* cell was the *bacillus subtilis* cell GalliPro®.

GalliPro® was mutagenized to get a pool of new individual *bacillus* cells. Spores were made and selected for rapid germination and outgrowth from spore to vegetative cell in presence of a bile salt medium comprising 4 and 6 mM bile salt a described in example 1 above.

*Bacillus subtilis* cell DSM 19467 was selected.

Table 1 below shows germination and outgrowth data. Time (hours) from $10^8$ CFU/ml corresponding to OD 0.2-0.3 until OD 0.4 is reached (mean of 3 replicates).

| B. subtilis | 4 mM bile | 6 mM bile |
|---|---|---|
| Existing product GalliPro ® (DSM 17231) | >20 | >20 |
| Bile tolerant and phytase overexpressing (DSM 19489) | 13 h 40 m | 15 h |
| Commercial product: Calsporin | >20 | >20 |

Selection of bile tolerant and phytase overexpressing DSM 19489 is described in example 4 below. DSM 19467 has germination and outgrowth roughly as DSM 19489.

CONCLUSION

DSM 19489 and DSM 19467 are bile resistant strains and clearly germinating and out-growing faster than GalliPro®.

Example 4

Selection of High Phytase Producing *bacillus* cells DSM 19489 (Classical) and DSM 19466 (GMO)

The starting *bacillus* cell was the *bacillus subtilis* cell DSM 19467 selected in example 3.

DSM 19467 was mutated by classical mutation to get a pool of new individual *bacillus* vegetative cells. The vegetative cells were selected for producing high amount of phytase by using the phytase assay described in example 2 above. High phytase producing *bacillus subtilis* cell DSM 19489 (classical) was selected.

The promoter of phytase in the strain DSM 19467 was exchanged with another *bacillus* promoter making it a high producer of phytase enzyme and thus DSM 19466 (GMO) was obtained.

Results of Phytase Measurements

| Strains | |
|---|---|
| DSM 19489 | *Bacillus subtilis* bile resistant and high phytase producing |
| DSM 19467 | *Bacillus subtilis* bile resistant mother strain of DSM 19489 |
| DSM 19466 | *Bacillus subtilis* bile resistant and genetically modified gene encoding for phytase (high phytase producer) |

TABLE 2

Results of phytase produced by the selected strains measured as described in example 2 above.

| Time (hours) | 4 | 6 | 8 | 24 |
|---|---|---|---|---|
| DSM 19489 | 2.68 | 0.83 | 1.06 | 0.44 |
| DSM 19467 | 1.10 | 0.57 | 0.68 | 0.59 |
| DSM 19466 | 2.30 | 1.07 | 1.37 | 0.44 |

Strain DSM 19489 produces 2.68 units of phytase as compared to 1.10 unit for DSM 19467 (which is the reference bile resistant mother strain). A similar level as DSM 19489 is achieved by the genetically modified strain DSM 19466 bile resistant (2.30) and is thus also a high phytase producer.

CONCLUSION

DSM 19489 is bile resistant and a high phytase producing *bacillus* cell and in this example produces 2 times more phytase as compared to DSM 19467, after 4 hours growing in the medium.

DSM 19466 (GMO) is the bile resistant strain, where the gene phytase is genetically modified to be a high producer of phytase, and similar to DSM 19489 it produces 2 times more phytase as the mother strain (DSM 19467), measured after 4 hours of growing in the medium.

DSM 19467 is originating from GalliPro and is not selected for high phytase production. Accordingly, it is believed that GalliPro® produces roughly the same amount of phytase as DSM 19467.

Example 5

Bile Resistance "Check" of High Phytase Producing *bacillus* Cells DSM 19489 (Classical) and DSM 19466 (GMO)

The high phytase producing *bacillus* cells DSM 19489 (Classical) and DSM 19466 (GMO) selected in example 4 were re-checked for their ability of rapid germination and outgrowth from spore to vegetative cells as described in example 1.

The results were that both DSM 19489 and DSM 19466 had maintained roughly the same good rapid germination and outgrowth as the starting cell DSM 19467 used to obtain them.

REFERENCES

1. Antonie Van Leeuwenhoek. 2006 August; 90(2):139-46. Epub 2006 Jul. 4
2. US2003/0124104A
3. U.S. Pat. No. 6,255,098

The invention claimed is:
1. A *Bacillus* cell selected from the group consisting of:
  (a) a mutant obtained from a *Bacillus subtilis* cell with registration number DSM 19467; and
  (b) a *Bacillus subtilis* cell with registration number DSM 19466 or a mutant thereof, wherein the mutant of (a) and the mutant of (b) exhibit
    (i) a vegetative cell growth point of 0.4 $OD_{630}$ after less than 18 hours and 19 hours in the presence of a 4 mM bile salt medium and a 6 mM bile salt medium, respectively, and
    (ii) phytase production in an amount of at least 1.25 times more than *Bacillus* cell DSM 19467 after incu- bating for 4 hours at 37° C. in a non-selective heart infusion broth, and each of the 4 mM bile salt media and the 6 mM bile salt media comprises non-selective veal infusion broth medium supplemented with a bile salt mixture comprising 60% taurodeoxycholate, 30% glycodeoxycholate and 10% deoxycholate.

2. The *Bacillus* cell of claim 1, which is said mutant of (a).

3. The *Bacillus* cell of claim 2, wherein the *Bacillus* has registration number DSM 19489 or is a mutant thereof.

4. The *Bacillus* cell of claim 1, which is a *Bacillus subtilis* cell with registration number DSM 19466.

5. The *Bacillus* cell of claim 1, which is a mutant of a *Bacillus subtilis* cell with registration number DSM 19466.

6. A *Bacillus* cell with registration number DSM 19489 or a mutant thereof, wherein the mutant exhibits
   (i) a vegetative cell growth point of 0.4 $OD_{630}$ after less than 18 hours and 19 hours in the presence of a 4 mM bile salt medium and a 6 mM bile salt medium, respectively, and
   (ii) phytase production in an amount of at least 1.25 times more than *Bacillus* cell DSM 19467 after incubating for 4 hours at 37° C. in a non-selective heart infusion broth, and each of the 4 mM bile salt media and the 6 mM bile salt media comprises non-selective veal infusion broth medium supplemented with a bile salt mixture comprising 60% taurodeoxycholate, 30% glycodeoxycholate and 10% deoxycholate.

7. The *Bacillus* cell of claim 6, wherein the *Bacillus* has registration number DSM 19489.

* * * * *